United States Patent
Dumont et al.

(12) 
(10) Patent No.: US 6,726,671 B2
(45) Date of Patent: Apr. 27, 2004

(54) CELL STORAGE MAINTENANCE AND MONITORING SYSTEM

(75) Inventors: Larry Joe Dumont, Arvada, CO (US); Frank Corbin, III, Littleton, CO (US)

(73) Assignee: Gambro, Inc., Lakewood, CO (US)

( * ) Notice: Subject to any disclaimer, the term of this patent is extended or adjusted under 35 U.S.C. 154(b) by 321 days.

(21) Appl. No.: 09/971,744

(22) Filed: Oct. 4, 2001

(65) Prior Publication Data

US 2002/0040216 A1 Apr. 4, 2002

Related U.S. Application Data

(63) Continuation-in-part of application No. 09/136,547, filed on Aug. 19, 1998, now Pat. No. 6,315,767.

(51) Int. Cl.[7] .................. A61B 19/00; A61M 37/00; B65D 33/14; B65D 30/22
(52) U.S. Cl. .............. 604/408; 604/404; 604/6.15; 383/1; 383/38; 128/DIG. 24
(58) Field of Search ................... 604/404, 408, 604/403, 409, 410, 890.1, 891.1, 892.2, 6.15; 383/1, 5, 38, 127, 105, 109; 220/500, 42.11, DIG. 30; 128/DIG. 24; 436/8, 16, 17

(56) References Cited

U.S. PATENT DOCUMENTS

| | | | |
|---|---|---|---|
| 2,856,885 A | * | 10/1958 | Huyck et al. ............ 116/106 |
| 2,856,930 A | | 10/1958 | Huyck et al. |
| 4,655,763 A | | 4/1987 | Malcolm et al. |
| 4,832,034 A | | 5/1989 | Pizziconi et al. |
| 4,952,498 A | | 8/1990 | Waters |
| 5,026,342 A | | 6/1991 | Hammerstedt et al. |
| 5,051,360 A | | 9/1991 | Waters |
| 5,071,760 A | * | 12/1991 | Watanabe et al. .......... 435/394 |
| 5,197,976 A | | 3/1993 | Herweck et al. |
| 5,261,870 A | * | 11/1993 | Hammerstedt et al. ....... 600/35 |
| 5,291,887 A | | 3/1994 | Stanley et al. |
| 5,401,376 A | | 3/1995 | Foos et al. |
| 5,583,162 A | | 12/1996 | Li et al. |
| 5,653,922 A | | 8/1997 | Li et al. |
| 5,709,653 A | | 1/1998 | Leone |
| 5,770,705 A | | 6/1998 | Shanbrom |

FOREIGN PATENT DOCUMENTS

| | | |
|---|---|---|
| EP | 0367337 | 5/1990 |
| EP | 0562303 | 9/1993 |
| EP | 0 909 555 A1 | 4/1999 |
| JP | 4-167756 | 6/1992 |
| WO | WO 92/19284 | 11/1992 |
| WO | WO 93/15402 | 8/1993 |
| WO | WO 95/33553 | 12/1995 |
| WO | WO 98/35228 | 8/1998 |

OTHER PUBLICATIONS

PCT Notification of Transmittal of the International Search Report or the Declaration, Form PCT/ISA/210 and 220; International Application No. PCT/US99/18920, Filing date Aug. 18, 1999 (Mailed Dec. 22, 1999).

Monotech, "too precious to wast", Safe–T–Vue, p. 1183, date unknown.

(List continued on next page.)

*Primary Examiner*—Patricia Bianco
(74) *Attorney, Agent, or Firm*—Laura M. Butterfield; Edna M. O'Connor

(57) ABSTRACT

A cell storage maintenance and monitoring system includes a blood product storage container, such as a flexible bag, and a microporous membrane which may be attached to an inner wall of the blood storage container to form a contained space between the inner wall and the membrane. The membrane includes a plurality of pores, preferably filled with an erodible substance responsive to a selected characteristic of the blood product.

19 Claims, 3 Drawing Sheets

OTHER PUBLICATIONS

Richard P. Batycky et al., "A Theoretical Model of Erosion and Macromolecular Drug Release from Biodegrading Microspheres", Journal of Pharmaceutical Sciences, vol. 86, No. 12, Dec. 1997, pp. 1464–1477.

Harry R. Allcock, "Cross–Linking Reactions for the Conversion of Polyphosphazenes into Useful Materials", Chem. Mater., vol. 6, No. 9, 1994, pp. 1476–1491.

Harry R. Allcock, "Water–Soluble Polyphosphazenes and their Hydrogels", Chapter in Hydrophilic Polymers (J.E. Glass, ed.) ACS Advances in Chemistry Series, 24B, 1995.

R. Langer, "Polymeric Delivery Systems for Controlled Drug Release", Chem. Eng. Commun., vol. 6, pp. 1–48, 1980.

Robert Langer, "Polymer–Controlled Drug Delivery Systems", ACC.Chem. Res., 1993, 26, 537–542.

* cited by examiner

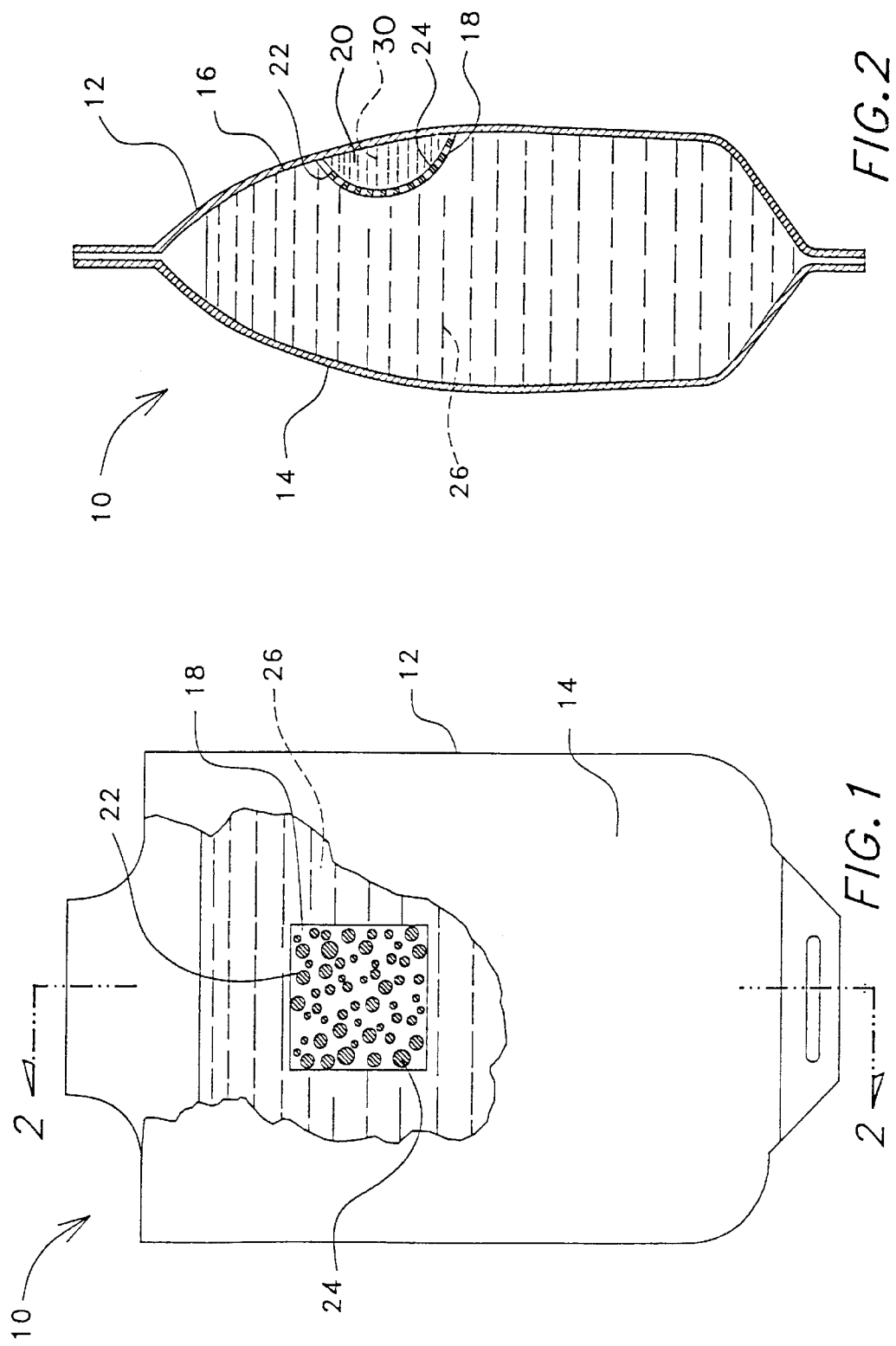

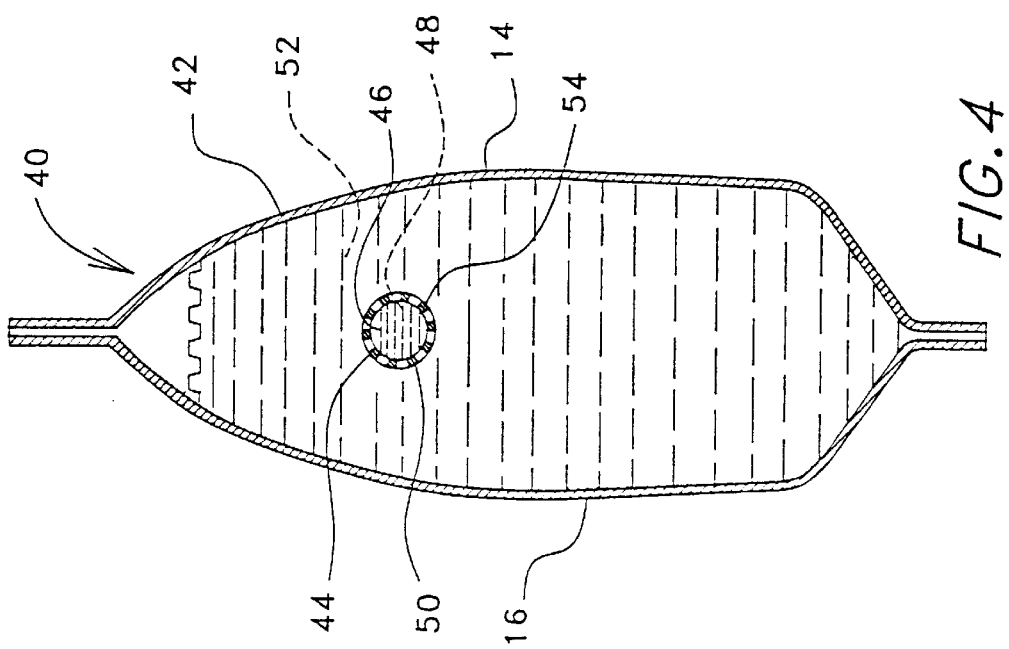
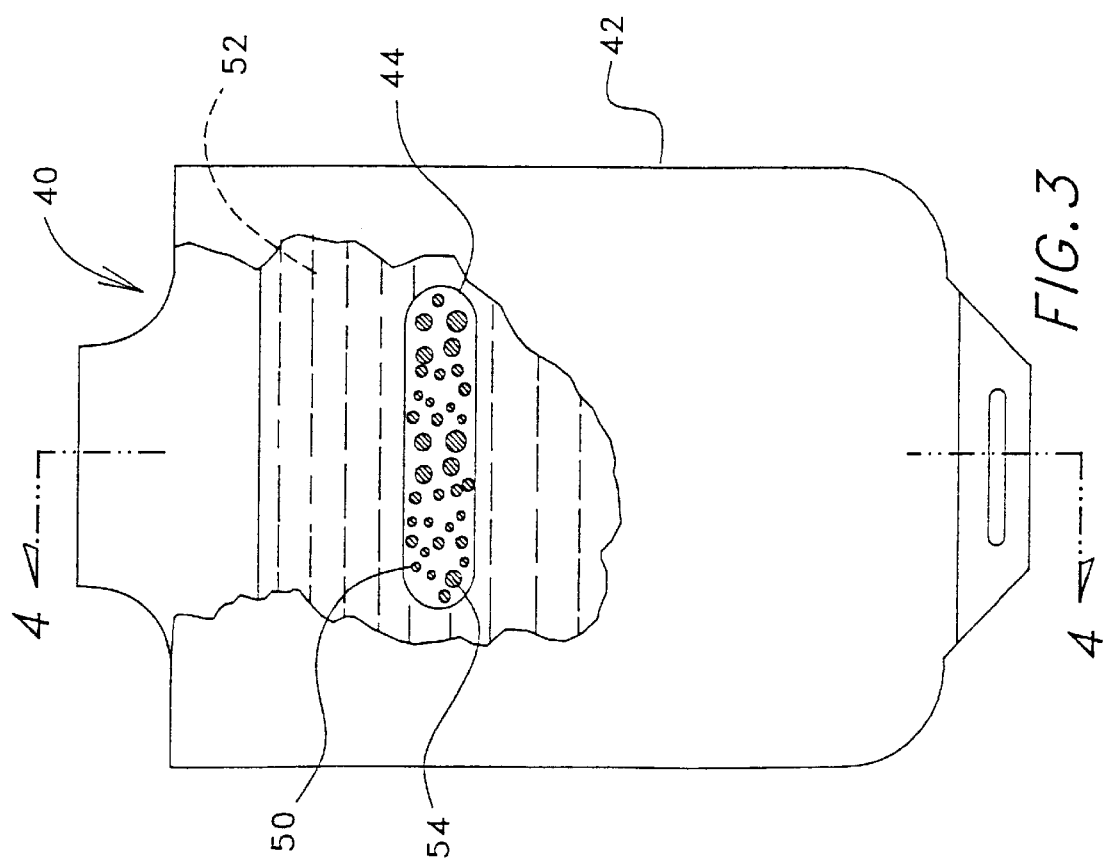

CELL STORAGE MAINTENANCE AND MONITORING SYSTEM

This application is a continuation-in-part of application No. 09/136,547, filed Aug. 19, 1998, now issued as U.S. Pat. No. 6,315,767.

FIELD OF THE INVENTION

The present invention relates generally to blood product storage containers, and more particularly, relates to an improved container for the storage of blood products which includes a microporous membrane for detecting and indicating changes in selected characteristics of the blood product contained therein and for preserving selected storage conditions.

BACKGROUND OF THE INVENTION

In the medical field, it is critical that a supply of various blood products, such as platelets, plasma, and red blood cells, be readily available. Such products are preferably stored for immediate use, generally in flexible bags which can be easily attached to blood tubing sets for use by the patient.

Often, however, blood products are stored for periods of time before use. During these storage periods, environmental factors may cause the quality of the blood product to be affected, making the use of the blood product questionable or inadvisable. For instance, changes in temperature, changes in the pH level of the blood product, and changes in the electrolyte balance of the blood product will compromise the quality of the blood product. Likewise, if bacteria have entered the storage container and contaminated the blood product, a decrease in glucose levels may be detected, or an increase in carbon dioxide production may be detected, indicating that the blood product is no longer of a useable quality.

Such changes in the quality of the blood product are generally undetectable by visual inspection. Instead, a sample of the blood product may have to be removed from the storage container and tested for assurance that the quality of the product is satisfactory.

Various devices have been created to address the problems associated with monitoring the quality of stored blood products. For example, the apparatus described in U.S. Pat. Nos. 4,952,498 and 5,051,360, both to Waters, are adapted to detect gas-generating activity of microorganisms in a storage vessel. A portion of the vessel inflates to indicate existence of an increase in pressure within the vessel, caused by microorganism activity, which is detectable by visual monitoring.

U.S. Pat. No. 5,514,106 to DÆSilva discloses a storage bag having means for indicating the status of the contents of the bag, specifically, whether the contents have been subjected to a treatment process, such as illumination or radiation sterilization. Overlapping portions of the bag form a flap having at least one hole punched therethrough which is capable of detection by a sensor to indicate treatment of the fluid within the bag. The bag may included a polarizing piece.

Likewise, the devices shown in WO92/19284 and JP406007410 each disclose blood storage bags having indicia that visibly change when irradiated to indicate that the contents have been exposed to radiation.

U.S. Patent No. to Malcolm et al discloses a testing and dispensing apparatus for measurement of the pH level of the contents contained in a storage vessel, comprising a dispensing tube and standard pH indicator removably received within the tube.

U.S. Pat. Nos. 2,856,885 and 2,856,930 to Huyck et al each disclose temperature indicators for blood storage containers which specifically indicate whether the contents of a blood storage container have reached a temperature exceeding 50° F. The devices utilize a tube filled with a selected indicator liquid.

In a seemingly unrelated technical area, known as separation technology, plugged pore membranes have been employed with storage containers, specifically to preserve and maintain the contents stored therein. Generally, a plugged pore membrane is used to separate two substances, and consists of a membrane having a number of small and larger pores plugged with selected polymers. The polymers are erodible upon exposure to certain environmental conditions. Erosion of the polymer allows one of the substances to pass through the membrane, depending on the size of the pores from which the polymer was eroded, thereby treating the second substance and preventing spoilage and promoting preservation.

As U.S. Pat. No. 5,261,870 to Hammerstedt et al discloses, suitable applications include cell cultures and cryobiology, preingestion preservation and storage of food and pharmaceuticals, shelf-life extension of polymers, proteins and other products, and the containing, transporting and dispensing of active agents, including cells, herbicides, pesticides, fertilizers, and cell growth nutrients or other biologically active agents for use in laboratory or industrial settings. The Hammerstedt separation barrier is specifically contemplated for the preservation of rooster and turkey sperm for use in commercial artificial insemination applications.

Erodible polymers and microspheres have been employed in the pharmaceutical industry, specifically, in dissolvable capsules and even silicon rubber compounds, from which a drug is slowly released and administered to a patient over periods of hours or days as the polymer is dissolved by exposure to certain substances or environmental factors.

None of the above described art, however, has addressed the problem of conveniently monitoring and sustaining the quality of stored blood products by incorporating a responsive, microporous membrane into a blood storage container. Accordingly, a need exists for a blood storage bag adapted to detect and indicate changes in selected characteristics of blood products, and for a storage bag which also may initiate the addition of buffers and nutrients to the product when needed to sustain or improve the quality of the product, preventing spoilage and waste.

SUMMARY OF THE INVENTION

In order to meet the aforementioned needs, it is an important aspect of the present invention to provide a flexible bag for the storage of blood products, including a membrane either attached to an interior surface of at least one of the walls of the flexible bag to define a contained space between the membrane and the wall, or free-floating within the inner volume of the bag. The contained space may contain a selected chemical agent.

The membrane has a plurality of pores therein to allow passive communication between the contained space or the agent and the blood product. In the preferred embodiment, the pores are filled with an erodible substance, such as a powder, which is responsive to a selected characteristic of the blood product, causing the pores to have a relatively smaller pore size at a first value of the selected characteristic and a relatively larger pore size at a second value of the selected characteristic.

It is also contemplated that the membrane itself may be composed of a material responsive to the selected characteristic of the blood product, such that the unfilled pores themselves are responsive to the selected characteristic, having a relatively smaller pore size at a first value of the selected characteristic and a relatively larger pore size at a second value of the selected characteristic.

It is yet another aspect of the present invention to provide the flexible bag described above in which the selected characteristic is pH level, where a fully closed pore state preferably occurs when the pH of said blood product is 6.4 or greater, and where the fully opened pore state occurs when the pH of said blood product is 6.2 or less.

It is a still further aspect of the present invention to provide a flexible bag as described above wherein the blood product is treated with buffers or nutrients when the pores begin to open, or the erodible substance begins to dissolve, in response to changes in the selected characteristic to preserve and maintain the quality of the blood product.

It is another aspect of the present invention to provide a method for monitoring the quality of a blood product stored in a flexible bag, including the steps of providing a membrane having a plurality of pores within the inner volume of said bag, and adding a selected chemical agent to said contained space, the agent in passive communication with said blood product through said pores.

It is a further aspect of the present invention to provide an improved apheresis system and an apheresis system tubing set including the above described flexible bag and microporous membrane attached to an interior surface of at least one wall of the flexible bag or free-floating within the contents of the bag.

BRIEF DESCRIPTION OF THE DRAWINGS

FIG. 1 is a partially broken away elevational view of the embodiment of the cell storage maintenance and monitoring system of the present invention, showing the microporous membrane patch attached to an inner wall of the flexible bag;

FIG. 2 is a cross-sectional view of embodiment of the cell storage maintenance and monitoring system of the present invention shown in FIG. 1, showing the microporous membrane patch attached to an inner wall of the flexible bag;

FIG. 3 is a partially broken away elevational view of another embodiment of the cell storage maintenance and monitoring system, showing a microporous membrane pod or capsule within the inner volume of the bag, unattached to the flexible bag;

FIG. 4 is a cross-sectional view of the embodiment shown in FIG. 3, illustrating the microporous membrane pod or capsule within the inner volume of the bag, unattached to the flexible bag;

DETAILED DESCRIPTION OF THE PREFERRED EMBODIMENTS

Figure 5:
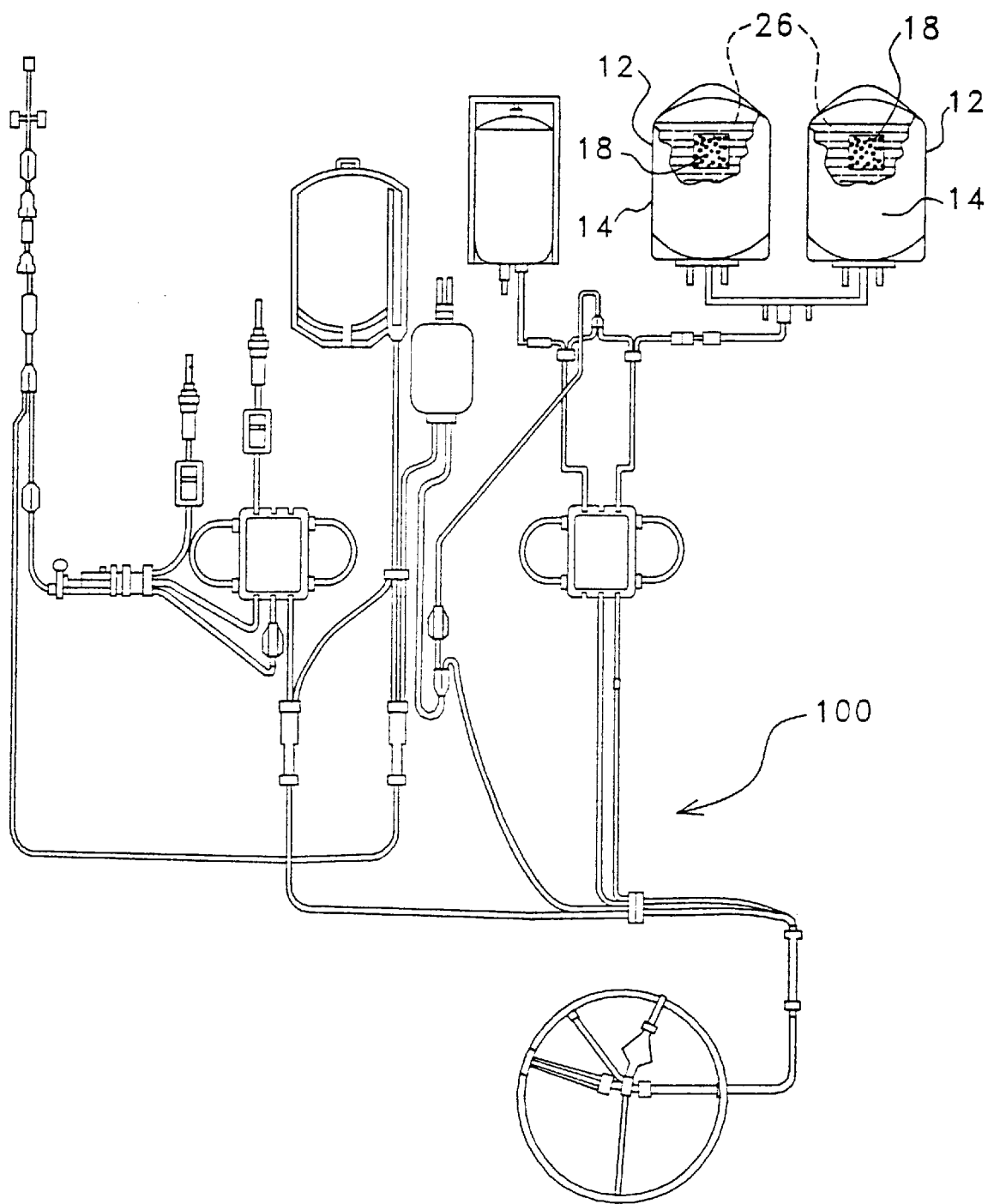
FIG. 5 is a partially pictorial, partially schematic representation of an apheresis system tubing set utilizing the microporous membrane patch within the flexible bag.

Referring next to the accompanying figures wherein the reference numerals connote the features described herein, FIGS. 1 and 2 illustrate a first embodiment of the cell storage maintenance and monitoring system 10 of the present invention.

The system 10 broadly comprises a blood storage container, illustrated in the accompanying figures as a flexible blood product storage bag 12, typically utilized to store and administer blood products such as plasma, platelets, red blood cells and the like. However, it is contemplated that other blood storage containers may also be employed in the present invention with the same results, and need not be in the form of a bag, or be flexible, plastic, or gas permeable.

The bag 12 has first and second walls 14, 16 joined at their peripheral edges. It is also contemplated that other types of bags may be used, such as the type of bag that is extruded, and one or both ends sealed before and/or after the contents are added to the bag. A membrane portion or patch 18 is attached to at to an interior surface of at least one of the walls 14, 16, forming a contained space 20 between the membrane patch 18 and the wall 14, 16. The membrane patch 18 contains a plurality of pores 22 of varying sizes.

The pores are preferably filled with an erodible substance 24, which is responsive to, and eroded upon exposure to, certain environmental conditions such as a change in pH, increased carbon dioxide levels, decreased glucose levels or changes in electrolyte levels, or a selected characteristic of a blood product 26 contained within the inner volume of the bag 12, such as a pH level or decreased glucose levels. Such environmental conditions may be caused by bacteria contained within the blood. The erodible substance is preferably a polymer material such as those found in the family of phosphohydrazines, and may have a powder-like consistency.

Recent revisions to standards established for the storage of blood products require that platelets be suspended in sufficient plasma so that the pH determined at the temperature of storage shall be 6.2 or greater in the units tested at the end of the allowable storage interval. It is contemplated that the erodible substance 24 contained within the pores 22 begins to dissolve when the pH of the stored blood product drops to 6.4 and is completely eroded away when the pH of the blood product reaches 6.2 (at 22° C.). Accordingly, the pores 22 will open or enlarge as the pH level of the blood product falls.

The contained space 20 may or may not contain a selected chemical agent or indicator 30. When the contained space 20 does not contain a chemical agent or indicator 30, upon opening or enlargement of the pores 22, portions of the blood product 26 may pass through the pores 22 into the contained space 20 and be detectable upon visible inspection by medical personnel, indicating that the pH level has dropped and the quality of the blood product has been compromised.

When the contained space 20 does contain a chemical agent or indicator 30, it is contemplated that either a portion of the blood product 26 will pass into the contained space 20 to contact the indicator 30, which will change colors or otherwise provide a means for visually detecting the change in the product. In the alternative, the agent 30 may pass through the pores 22 into the blood product 26, causing a change to the color of the product 26 or otherwise indicating a change in the pH level of the blood product by visual examination.

The selected pore size, as well as the respective molecular sizes of the blood product or chemical agent, indicator, will determine which substance passes through the pores 22.

It is also contemplated that the contained space 20 may contain buffers and/or nutrients. In this situation, the erodible substance 24 will begin to dissolve when the pH level reaches 6.8, and will be completely dissolved when the pH level reaches 6.5 (at 22° C). Upon eroding of the substance 24 and enlargement of the pores 22, the buffers or nutrients pass from the contained space 20 through the pores 22 and into the blood product 26. The buffers and/or nutrients are preferably sodium bicarbonate, sodium phosphate, sodium acetate, and fatty acids, or other salts of bicarbonate, phosphate, acetate, and fatty acids, which serve to maintain a higher quality of blood product, extend the shelf life of the product and prevent waste. It is also contemplated that two or more patches could be used. For example, a first patch could create a contained space including an indicator, while a second patch could create a contained space including buffers or nutrients.

As noted above, the membrane patch 28 shown in FIGS. 1 and 2 is attached at its peripheral edges to an inner wall 16 of the flexible bag 12 to form the contained space 20 between the patch and the wall 16. It is also contemplated that two or more patches could be used. The pores 22 are thus exposed to both the blood product 26 and the contained space 20 and/or the agent or indicator contained therein. The patch 18 may be attached to the bag by a variety of known welding methods, including radio frequency, solvents, heat, or ultra-violet-activated adhesive.

In the embodiment shown in FIGS. 3 and 4, the cell storage maintenance and monitoring system 40 is similar in most respects to the embodiment described above with reference to FIGS. 1 and 2. As illustrated in FIGS. 3 and 4, the membrane may be in the form of one or more pods or capsules 44, and is free-floating within the contents of the blood bag 42, rather than affixed as a patch to an inner wall of the bag 42. The pod or capsule 44 includes a contained space 46 surrounded by the membrane which may contain a chemical agent, an indicator, buffers or nutrients 48 in the manner described above with reference to FIGS. 1 and 2. The outer surface of the membrane capsule 44 contains a plurality of pores 50 of varying sizes, which are adapted to allow passive communication between the contained space 46 and the blood product 52.

The pores 50 may be filled with an erodible substance 54, which is reactive and dissolvable upon exposure to certain environmental conditions or to a selected characteristic of the blood product, such as pH. Preferably, the erodible substance is a polymer material from the family of phosphohydrazines. The substance begins to erode when the pH drops to a selected value, 6.4, as described above with references to FIGS. 1 and 2, causing the pore size to begin enlarging and to continue to enlarge until the substance is completely eroded at pH 6.2. When the pores are thus in this "open" state, the blood product and chemical agent or indicator, if one is present, may pass through the pores to act as a visual indicator, in the manner described above.

The present invention may also take the form of a microporous tablet or disc. The disc includes a molded cup, made of vinyl or another, similar polymer, an chemical agent, such as a powder-like material as above described with reference to the other embodiments, contained within the cup, and a plugged, microporous membrane cap or lid heat-sealed onto the cup. As with the embodiments described with reference to FIGS. 1 through 4, the disc may either be affixed to the inside wall of the blood storage container or free-floating within the contents of the container. The disc and the microporous membrane cap thus operate in the manner described with reference to the patch and pod embodiments, such that the filled pores are responsive to changes in a selected characteristic of the surrounding blood product, such as pH.

It is also contemplated that the membrane and thus the pores themselves, in both of the embodiments shown in FIGS. 1 through 4, may be made up of a material that is responsive to changes in pH or other characteristic of the blood product, such that the pore size will actually increase, or the pores will "open", when the pH or other characteristic reaches a certain value.

The present invention also contemplates the use of erodible systems other than the above described plugged pore membrane patch and capsule. For instance, an erodible capsule or tablet made of the pH responsive substance, preferably selected from the family of phosphohydrazines, could also be employed as a pH indicator or as a means to release indicators, buffers and/or nutrients to blood products to maintain their quality.

The standard blood storage bag (ELP bag) contemplated for use in the present invention is typically fabricated from a polyvinylchloride film plasticized with n-butryltri-n-nexyl-citrate (B6). The film is nominally 0.015 inch with 39% B6 by weight. The final disposable bag is sterilized, and typically has a shelf life of two years from the date of sterilization. Platelets are commonly stored in plasma or in a plasma/crystalloid solution at 20° to 24° C. with constant gentle agitation.

The above described cell storage maintenance and monitoring system is intended for use with a variety of blood products, including in the collection of whole blood, and for the storage of platelets, plasma, red blood cells (RBCs), or stem cells.

Further, the present invention is contemplated for use in various other applications are also contemplated. For example, changes in pH levels may be one indicator of bacterial contamination. A secondary indicator, such as a glucose level detector, or carbon dioxide detector, coupled with the above described system, is contemplated, and may also employ a means to destroy the bacteria, such that an appropriate chemical agent is released through the opened pores to treat the blood product.

Other applications for cell storage include a potassium ion or free hemoglobin sensor to detect excessive red blood cells lysis or leakage; electrolyte detection, pH indication, such as that described above, both as a simple indicator and/or as a trigger for addition of supplemental fuels, buffers, electrolytes or other reagents, such as glucose or phosphate; and an adenosine triphosphate (ATP) concentration indicator like the pH indicator described above, either as a quality indicator or for reagent delivery.

Applications for stem cell storage include the pH change indicator and bacterial detection methods described above. Applications for plasma storage may also include the pH change indicator described above and a freeze-thaw-freeze indicator.

A method of monitoring the quality of stored blood products is also contemplated, including the steps of providing a porous membrane having a contained space to the inner volume of a flexible storage bag. The contained space may or may not contain a chemical agent or detector, in the manner described above.

The present invention is also intended for use in apheresis systems and disposable apheresis tubing sets 100, as shown in FIG. 5, which typically employ the flexible blood product storage bag 12, which is a part of this invention. Specifically, disposable components such as flexible bags, reservoirs, sources of therapeutic fluids, oxygenators, dialyzers, pumps, and so on, are used with medical apparatus such as a blood component separation device, a dialysis apparatus, or a heart/lung apparatus for use in open heart surgery. The cell storage maintenance system of the present invention is contemplated for use with these systems, and in particular, with an apheresis system such as the COBE Spectra® apheresis system and COBE Trima® apheresis system, which are similar to the system 100 pictured in FIG. 5, and use one or more blood storage bags 12.

It is therefore to be understood that while preferred forms of the present invention have been herein set forth and described, various modifications and changes may be made in the construction and arrangement of parts and steps, as well as composition of materials without departing from the spirit and scope of the present invention as defined by the appended claims.

What is claimed is:

1. A flexible bag for the storage of blood products having first and second walls joined at their peripheral edges to define an inner volume of said bag, comprising:

a membrane attached to an interior surface of at least one wall of the flexible bag thereby defining a contained space, said membrane having a plurality of pores therein to allow passive communication between said contained space and the blood product, said pores being filled with an erodible substance responsive to a selected characteristic of said blood product, said erodible substance being erodible in response to a selected characteristic of the blood product to define a relatively smaller pore size and a fully closed pore state at a first value of the selected characteristic and a relatively larger pore size at a second value of the selected characteristic.

2. A flexible bag according to claim 1 wherein said contained space is adapted to contain a selected chemical agent, and wherein said pores allow passive communication between said agent and said blood product at selected characteristics of the blood product.

3. A flexible bag according to claim 2 wherein the selected chemical agent comprises buffers or nutrients for storage of blood products.

4. A flexible bag according to claim 2 wherein said selected chemical agent is a potassium ion or free hemoglobin sensor.

5. A flexible bag according to claim 2, wherein said selected chemical agent is a freeze-thaw-freeze indicator.

6. A flexible bag according to claim 1 wherein the relatively larger pore size allows at least a portion of said agent or said blood product to pass through said pores, representing a fully opened pore state.

7. A flexible bag according to claim 6 wherein the fully opened pore state occurs when the pH of said blood product is about 6.5 or less.

8. A flexible bag according to claim 1 wherein:

the selected characteristic has a range of values which includes the first value and the second value and values between the first and second values; and the pore size is between the fully opened pore state and the fully closed pore state at values of the selected characteristic between the first and second values.

9. A flexible bag according to claim 8 wherein the fully opened pore state occurs when the pH of said blood product is about 6.2 or less.

10. A flexible bag according to claim 1 wherein the fully closed pore state occurs when the pH of said blood product is about 6.4 or greater.

11. A flexible bag according to claim 1 wherein the fully closed pore state occurs when the pH of said blood product is about 6.8 or greater.

12. A flexible bag according to claim 1 further comprising an indicator in said contained space adapted to enhance user observation of a relatively larger pore size.

13. A flexible bag according to claim 1 further comprising an indicator in said contained space for detection of change in the glucose level of said blood product for detection of bacterial contamination.

14. A flexible bag according to claim 1 further comprising an indicator in said contained space for detection of increased carbon dioxide in said blood product for detection of bacterial contamination.

15. A flexible bag according to claim 1 further comprising an indicator in said contained space for detection of changes in electrolytes in said blood product for detection of bacterial contamination.

16. A flexible bag according to claim 1 wherein the blood product is selected from the group consisting of whole blood, platelets, red blood cells, stem cells, and plasma.

17. A flexible bag according to claim 1 wherein said contained space is further defined by said at least one wall of the flexible bag.

18. A flexible bag for the storage of blood products having first and second walls joined at their peripheral edges to define an inner volume of said bag, comprising:

a membrane contained within the inner volume of said bag and defining a contained space having a selected chemical agent therein, said membrane having a plurality of pores therein to allow passive communication between said agent and the blood product, said pores selectively containing an erodible substance, said erodible substance being erodible in response to a selected characteristic of a blood product contained in said bag to define a relatively smaller pore size at a first value of the selected characteristic and a relatively larger pore size at a second value of the selected characteristic.

19. An apheresis system tubing set including a flexible bag having first and second walls joined at their peripheral edges to define an inner volume, comprising:

a membrane attached to an interior surface of at least one of said first and second walls of the flexible bag thereby defining a contained space, said space adapted to contain a selected chemical agent, said membrane having a plurality of pores therein to allow passive communication between said agent and the blood product, said pores being filled with an erodible substance responsive to a selected characteristic of said blood product, said erodible substance being erodible in response to a selected characteristic of the blood to define a relatively smaller pore size at a first value of the selected characteristic and a relatively larger pore size at a second value of the selected characteristic.

* * * * *